(12) United States Patent
Horn et al.

(10) Patent No.: US 6,698,470 B1
(45) Date of Patent: Mar. 2, 2004

(54) METHOD AND DEVICE FOR COLLECTING FRACTIONS AFTER MATERIAL SEPARATION

(75) Inventors: Anton Horn, Jena-Woellnitz (DE); Stefan Kreusch, Golmsdorf (DE); Thomas Moore, Jena (DE); Guenther Sammler, Jena (DE); Guenter Ditze, Stadtroda (DE)

(73) Assignee: CyBio Instruments GmbH, Jena (DE)

( * ) Notice: Subject to any disclaimer, the term of this patent is extended or adjusted under 35 U.S.C. 154(b) by 0 days.

(21) Appl. No.: 10/169,449

(22) PCT Filed: Feb. 8, 2000

(86) PCT No.: PCT/EP00/01002

§ 371 (c)(1),
(2), (4) Date: Jul. 1, 2002

(87) PCT Pub. No.: WO01/59424

PCT Pub. Date: Aug. 16, 2001

(51) Int. Cl.$^7$ .................................................. G01N 1/00
(52) U.S. Cl. .................... 141/130; 141/1; 141/13; 141/329; 422/63; 422/99; 73/863.01; 73/864.24; 73/864.35
(58) Field of Search .................. 141/1, 13, 130, 141/329; 222/420, 422; 422/63–67, 99, 103, 104; 73/863, 863.01, 864.24, 864.25, 864.34, 864.35, 864.62

(56) References Cited

U.S. PATENT DOCUMENTS

| | | | | |
|---|---|---|---|---|
| 4,022,059 A | * | 5/1977 | Schontzler et al. | 73/198 |
| 4,030,640 A | * | 6/1977 | Citrin et al. | 222/207 |
| 4,856,563 A | * | 8/1989 | Yamaguchi et al. | 141/1 |
| 5,216,926 A | * | 6/1993 | Lipscomb | 73/864.25 |
| 5,270,211 A | * | 12/1993 | Kelln et al. | 436/43 |
| 5,315,887 A | * | 5/1994 | Heitel | 73/864.11 |
| 5,413,000 A | * | 5/1995 | Stark et al. | 73/864.23 |
| 5,935,523 A | * | 8/1999 | McCandless et al. | 422/100 |
| 5,942,441 A | * | 8/1999 | Nylen | 436/179 |
| 5,947,167 A | * | 9/1999 | Bogen et al. | 141/1 |
| 5,969,272 A | * | 10/1999 | Tanaka | 73/864.24 |
| 6,045,755 A | * | 4/2000 | Lebl et al. | 422/65 |

FOREIGN PATENT DOCUMENTS

| | | | |
|---|---|---|---|
| EP | 0 795 742 | * | 9/1997 |
| EP | 0 884 575 | * | 12/1998 |
| WO | WO 91/01007 | * | 1/1991 |
| WO | WO 98/40159 | * | 9/1997 |

* cited by examiner

Primary Examiner—J. Casimer Jacyna
(74) Attorney, Agent, or Firm—Reed Smith LLP

(57) ABSTRACT

An airbag cover is defined by a predetermined breaking line which is introduced into a shaped flat material in a recessed manner. The recesses are achieved by removing material by means of laser radiation. According to the invention, the flat material is provided with a barrier layer. The barrier layer, by reason of its material properties, has greater resistance to removal of material by laser action than the material of the rest of the flat material. The recesses made by removing material extend along the predetermined breaking line in the flat material up to the barrier layer. The barrier layer makes it possible to produce a predetermined breaking line by means of laser machining which allows an exact residual wall thickness of the airbag cover in the area of the predetermined breaking line, so that the tearing strength can be adjusted very accurately, which is critically important for a reliable deployment of an airbag. Further, a method for the efficient production of an airbag cover of this type is indicated.

27 Claims, 6 Drawing Sheets

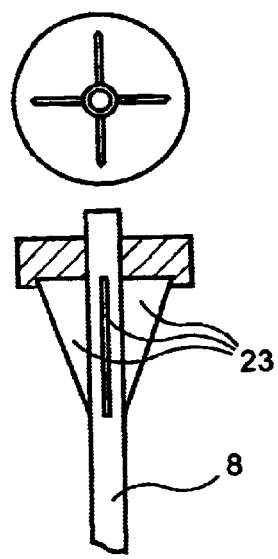
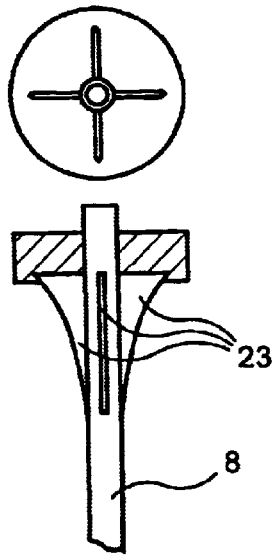
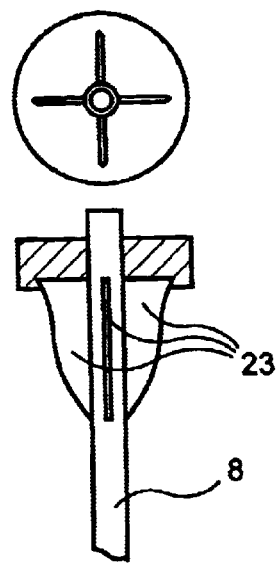
FIG. 6A  FIG. 6B  FIG. 6C
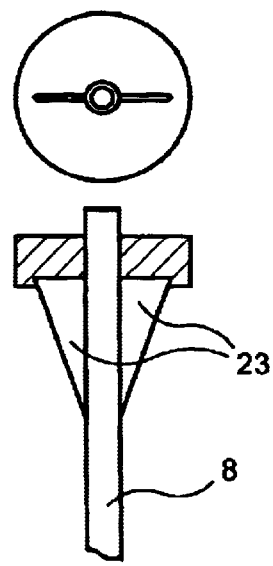
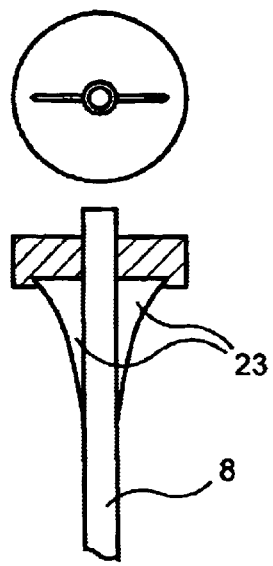
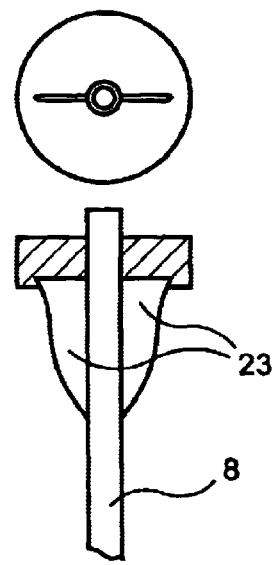
FIG. 6D  FIG. 6E  FIG. 6F

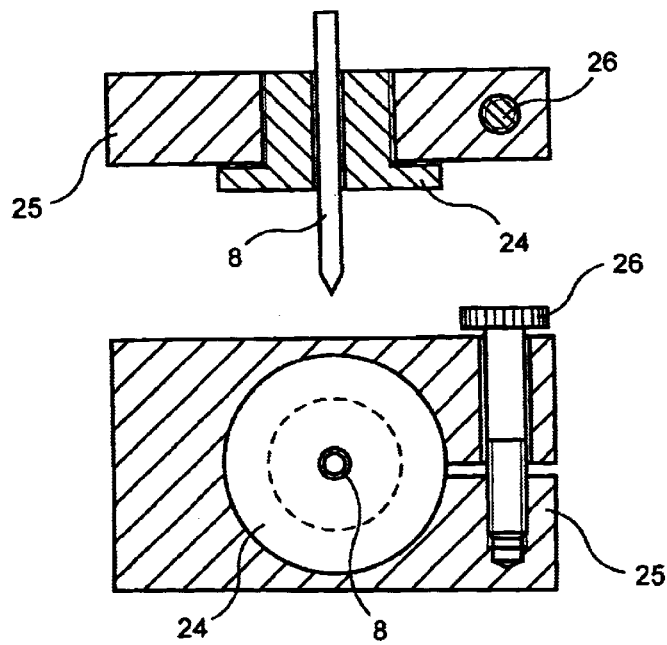
F I G. 7
| CONDITIONS | EVAPORATION RATE [μl / min] | MATERIAL LOSS OVER 18.4 h [%] |
|---|---|---|
| MULTIWELL ANALYSIS PLATE AT ROOM TEMPERATURE, OPEN | 5.22 | 60 |
| MULTIWELL ANALYSIS PLATE AT ROOM TEMPERATURE, WITH PERFORATED FOIL | 0.37 | 4.2 |
| MULTIWELL ANALYSIS PLATE AT 4 DEGREES C, WITH PERFORATED FOIL | 0.037 | 0.4 |
F I G. 8

METHOD AND DEVICE FOR COLLECTING FRACTIONS AFTER MATERIAL SEPARATION

CROSS-REFERENCE TO RELATED APPLICATIONS

This application claims priority of PCT Application Ser. No. PCT/EP00/01002, filed Feb. 8, 2000 the complete disclosure of which is hereby incorporated by reference.

BACKGROUND OF THE INVENTION a) Field of the Invention

The invention is directed to a method and a device for collecting fractions, preferably in microliter scale, and is provided for analytic and preparative applications in biochemistry, molecular biology, chemistry, pharmaceutics and pharmacology, but especially in biotechnology. By way of example, the invention can be used in active ingredient screening in the pharmaceutical industry, clinical chemical analysis, protein analysis after fragmentation and combinatorial chemistry.

b) Description of the Related Art

Over the last decade, methods for material separation, especially in chromatography, have developed considerably and undergone miniaturization. This miniaturization became necessary in particular because frequently only very small substance amounts in the $\mu$g range or mg range were available for routine characterization of many biologically active substances. Further, the requirements for specimen throughput in analysis, active ingredient screening, biotechnology and molecular biology have risen sharply in recent years. The level of pump, column and detection technique has made it possible to carry out separation in the range of a few microliters. Recently, in particular, in addition to online tracking of chromatography results, the need has arisen for offline analysis of individual fractions which are collected in high resolution in closely spaced grids (e.g., peptide separations before mass spectrometry: P. L. Courchesne, S. D. Patterson, "Manual microcolumn chromatography for sample cleanup before mass spectrometry", *Biotechnics* 22 (1998), No. 2: 244–250). The required close fractionation results in many individual specimens necessitating an effective parallel processing for purposes of high-resolution characterization.

However, the applied known chromatography separation methods are carried out sequentially and, therefore, for an effective parallel further handling, must be adapted to available grids for multipipetting dispensing and multichannel measurement technique. At present, a commonly used standard for specimen vessels is defined by the multiwell analysis plate, as it is called, and the grid derived from it (for example, N. S. Gerasimova, I. V. Steklova, T. Tuuminen, "Fluorometric method for phenylalanine microplate assay adapted for phenylketonuria screening", *Clin. Chem.*, October 1989 35 (10): 2112–2115; P. D. Matthews, E. T. Wurtzel, "High-throughput microplate format for producing and screening riboprobes from bacterial cells", *Biotechniques*, June 1995 18 (6): 1000–1002, 1004; P. Wu, S. Daniel-Issakani, K. LaMarco, B. Strulovici, "An automated high throughput filtration assay: application to polymerase inhibitor identification",*Anal. Biochem.*, Feb. 15, 1997, 245 (2): 226–230; M. S. Rashed, M. P. Bucknall, D. Little, A. Awad, M. Jacob, M. Alamoudi, M. Alwattar, P. T. Ozand, "Screening blood spots for inborn errors of metabolism by electrospray tandem mass spectrometry with a microplate batch process and a computer algorithm for automated flagging of abnormal profiles, *Clin. Chem.*, July 1997, 43 (7):1129–1141). The dimensions are determined by the SBS standard. Starting from these dimensions, deriving from a quantity of 96 specimen vessels, there are grid formats with 384, 864 and 1536 specimen vessels (catalogs of Greiner or Corning Costar). Almost all equipment for high specimen throughput in liquid handling and parallel handling is adapted to this grid format and is therefore compatible in the field.

The separating methods with liquid volume-moving separating techniques such as HPLC or FPLC which run sequentially collect the separated specimens with fraction collectors in a determined sequence or with a determined grid either continuously according to volume and time, according to a timed program or according to a predetermined threshold of the respective detector.

Various types of automatic fraction collectors, coupled with liquid separating processes which are often also automated, are known (U.S. Pat. No. 4,422,151; U.S. Pat. No. 4,049,031; or DE 3 520 055). They comprise holders for specimen vessels, a feed for the solution to be collected, and an internal or external control unit. The variants for the arrangement of specimen vessels are as follows: carrousel type (U.S. Pat. No. 3,838,719), spiral (U.S. Pat. No. 3,570, 555), rows and columns (U.S. Pat. No. 4,422,151), rows and columns in movable containers (U.S. Pat. No. 4,077,444).

The positioning of the specimen vessels under the outlet opening for the specimen solution is carried out either by a movement of the specimen vessel holder or by a movement of the outlet opening.

The collected volumes are in the lower range of 5 $\mu$l (brochure by Pharmacia Biotech: Fraktionssammler am Smart™ System). Formats corresponding to the grid of the multiwell analysis plate are often used for small volumes and high specimen numbers (INTERNET publication: Gilson, for fraction collector FC203, for fraction collector in the combinatorial chromatography system and for the $\mu$-fractionator based on a Gilson 221 XL). These fraction collectors have a holding capacity for at least one specimen container. A movable element guides the specimen feed horizontally over the individual specimen vessels fixed in the grid and fills them as prescribed. In addition to the horizontal positioning movement over the respective vessel, there are arrangements which move the feed element, a capillary or capillary tube, vertically into the vessel for depositing the specimen (INTERNET publication by Gilson for the fraction collector in combinatorial chromatography system and the $\mu$-fractionator based on a Gilson 221 XL, and by Pharmacia Biotech for the Smart™ System fraction collector). Another vertical movement for separating the last drop at the outlet is patented in DE 4 303 275.

Previous fraction collectors had disadvantages with respect to the small liquid quantities of the specimens, particularly evaporation losses (high surface-to-volume ratio), entrainment contamination between the fractions, airborne contamination such as dust particles and microorganisms, and possible aerosol formation in the collected material.

Reduced evaporation and improved conservation can be achieved by regulating the temperature to below room temperature (Gilson INTERNET publication for thermostatic specimen container in FC206 fraction collector).

Another possibility for reducing evaporation loss and preventing contamination consists in providing the plates with covers by gluing or welding, so that every specimen vessel on the plate is hermetically closed (U.S. Pat. No. 5,056,427; U.S. Pat. No. 5,604,130). Gilson uses a cover for preventing contamination of the collecting vessels in their FC 206 fraction collector. When covering with foil, there is also the possibility of gluing foils manually and of commercially available devices with automatic foil gluing and welding (INTERNET publication: Presto Automated Microplate Sealer by Zymark).

The drawback in all of these covers used for protecting against evaporation and contamination for fraction collector specimens consists in that the openings of the collecting vessels are primarily closed and the covers or foil must therefore be removed before collection and then replaced after collection. First of all, this represents increased labor in specimen handling, i.e., preparatory handling of the collecting vessels and follow-up handling for the collecting process. Second, it is particularly problematic that no sufficient protection is provided during the temporary absence of a closure during fractionation. Further, there is a risk of specimen loss, contamination and faulty fractionation, particularly due to entrainment of fractions, during fractionation. This also renders effective automation of the collecting process impossible. For these reasons, there is essentially no practical use for closure of the collecting vessels.

OBJECT AND SUMMARY OF THE INVENTION

It is the primary object of the invention to collect fractions in microliter scale without the risk of contamination, liquid losses, mixing up of fractions or aerosol formation and with the lowest possible expenditure on handling for prehandling and posthandling of specimen vessels.

According to the invention, the collecting vessels are closed by a cover which can be perforated, for example, an adhesive foil, or the collecting vessels can already be provided with a hermetic closure of this kind. When positioned, the cover is penetrated by a thin, hollow perforating tip and the fractionated liquid is dispensed through the cover into the selected collecting vessel when the collecting position is reached. The cover prevents the release of aerosol into the environment and seals the collecting vessels so as to protect against evaporation and contamination. Further, it substantially prevents faulty fractionation of substance proportions which, for example, drip onto the multiwell analysis plate into the collecting vessels thereof and are mixed with the collected fraction. After the specimen is dispensed, the hollow needle supplying the specimen moves back into its starting position over the collecting vessel. For reliable prevention of faulty fractionation, the supplying of the liquid to be fractionated to the perforating tip, as substance-dispensing element, is interrupted during the positioning movement of the perforating tip. This interruption is advantageously implemented by an electromechanical valve. The volume which flows in continuously in front of the valve is received by and temporarily stored in an elastic deformation body, preferably a thin elastic feed tube. Residual drops suspended from the perforating tip are deposited into the collecting vessel by wiping off at the vessel bottom or at the surface of the liquid which is to be collected or which has been dispensed and/or by an impulse for expelling the residual solution from the needle tip. The advantageous use of one possibility or the other depends on the specimen to be collected, the collecting vessels to be used and the collecting volume.

During fractionation, the collecting vessels remain closed with the exception of the tiny perforation opening, so that said protection against evaporation loss, contamination, aerosol formation in the environment, etc. is maintained during collection. It is not necessary to provide additional covering for protected conservation, transport and further processing of the fractions in the collecting vessels because, apart from the perforation puncture, the collecting vessels are still substantially covered after fractionation. The expenditure on handling for arranging the thin cover foil which can be perforated, e.g., an adhesive foil, on a multiwell analysis plate is low, and multiwell analysis plates which are covered already during manufacture can be used if required.

In the following, the invention is described more fully with reference to an embodiment example shown in the drawing.

BRIEF DESCRIPTION OF THE DRAWINGS

In the drawings:

FIG. 6 shows a perforating tip with additional cutters in different embodiment forms;

FIG 7 shows a clamping device for the perforating tip; and

FIG 8 shows a comparison of the evaporation losses in an open multiwell analysis plate and in a closed multiwell analysis plate.

DESCRIPTION OF THE PREFERRED EMBODIMENTS

Figure 1:
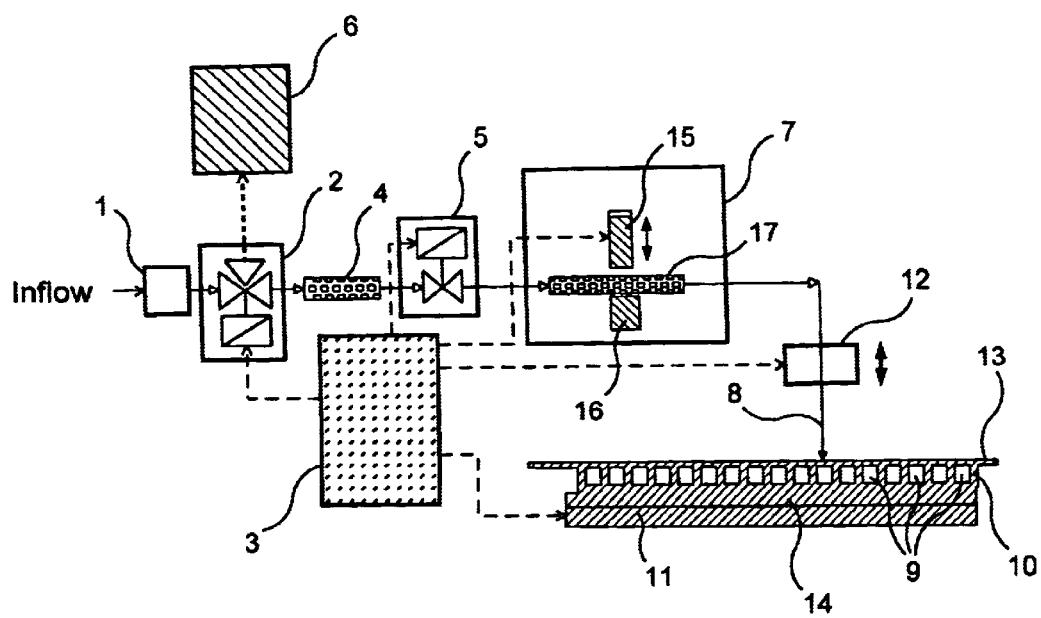
FIG. 1 shows the basic construction of the fraction collector.
Figure 2:
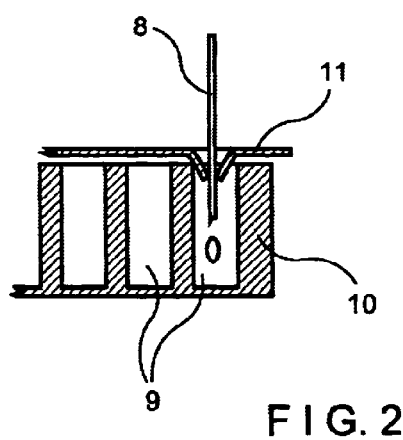
FIG. 2 shows a perforating tip in the collecting position after piercing the cover of the collecting vessel.

FIG. 1 shows the basic construction of the fraction collector in microliter scale. The substance to be fractionated is supplied to a multidirectional valve 2 via a connection adapter 1. The multidirectional valve 2 is controlled by a control unit 3 so as to direct the volume flow either to a waste receptacle 6 or through an elastic tube 4, a fractionating valve 5 and an expelling device 7 in direction of a hollow perforating tip 8 through which the fractions to be collected are dispensed in selected collecting vessels 9 of a multiwell analysis plate 10. For x-,y-positioning of the hollow perforating tip 8 relative to the collecting vessels 9, the multiwell analysis plate 10 communicates with a positioning unit 11, for example, an x-,y-coordinate table, known per se, whose movements are likewise controlled by tit control unit 3. By positioning the multiwell analysis plate 10 relative to the perforating tip 6, tie corresponding collecting vessel 7 of the multiwell analysis plate 10 is selected for each fraction by means of the control unit 3 and the positioning unit 11 Further, tie control unit 3 controls a lifting unit 12 for the z-movement of the perforating tip 8 so that, after a collecting vessel 9 is selected for the respective fraction, the perforating tip 8 can be moved into the collecting vessel 9 for dispensing the substance. During its vertical movement for reaching the collecting position for the dispensing of substance, the perforating tip 8 pierces a cover foil 13 arranged on the multiwell analysis plate 10 and dispenses the fraction into the selected collecting vessel 9 through the cover foil 13 which is perforated in this way (see FIG. 2).

The cover foil 13, for example, an adhesive foil, prevents aerosol formation in the surroundings, evaporation and contamination of the very small fraction volumes in the collecting vessels 9 by dust particles and dirt particles before, during and after fractionation. In the event that drops which exit from the perforating tip 8 that is moved into position over the collecting vessels 9 and which no longer belong to the respective fraction reach the multiwell analysis plate 10, for example, due to inadequate closing of the valves or leaky connections, these drops are also kept away from the collecting vessels 9 by the cover foil 13 and, therefore, can not cause faulty fractionation. For preventative protection against contamination and so that the collecting vessel 9 remain sterile, the multiwell analysis plate 10 can also be supplied, stored and provided for fractionation with this cover foil 13 already in place. It is also possible to place a solution or solid substance in the multiwell analysis plate 10, for example, stabilizers for proteins, to close the multiwell analysis plate 10 with the cover foil 13 and to collect the fractions in the collecting vessels 9 with the material placed therein.

For additional protection against evaporation, the multiwell analysis plate 10 communicates with a temperature-regulating unit 14, so that the collecting vessels 9 of the multiwoll analysis plate 10 which are arranged in a defined grid format, for example, n×8×12, are kept at a temperature below room temperature.

After the substance is dispensed, the perforating tip 8 is moved out of its collecting position in the collecting vessel 9 back into an upper starting position by z-positioning. Another collecting vessel 9 can then be selected for the next fraction to be collected.

During the positioning movement of the perforating tip 8 from or to its collecting position in the respective selected collecting vessel 9, including the relative positioning movement of the multiwell analysis plate 10, the volume flow which flows continuously through the multidirectional valve 2 is interrupted by the fractionating valve 5.

The tube 4 is elastic and has a small inner diameter (0.5 mm or less). On the one hand, this ensures damping of the pressure impulse occurring in the substance to be collected due to the closing of the fractionating valve 5 and, on the other hand, ensures that the substance to be fractionated is received and stored temporarily without substantial mixing of substances, for example, due to whirling, until the next dispensing of substance. A drop of liquid still located on the perforating tip 8 is expelled by an impulse of the expelling device 7. In FIG. 1, the expelling device 7 comprises a plunger 15 which is moved electromagnetically by the control unit 3 and which transmits a brief mechanical impulse against an abutment 16 to the elastic tube 17 after a substance has been deposited in the selected collecting vessel 9 by the perforating tip 8. The short impulse could also be effectively transmitted to the substance in the perforating tip 8 or to its feed in other ways, e.g., by other mechanical elements such as cams and levers, a piezoelectric element, ultrasound, compressed gas or vacuum. It is also possible to wipe off the residual drop at the surface of the collected substance and/or of the substance already deposited or at the inner wall of the collecting vessel 9 by contact. For this purpose, the lifting device 12 advisably has a high-resolution stepping drive for very accurate, sensitive movement control of the perforating tip 8 or communicates with such a drive (the alternative solutions mentioned above for the impulse generation of the expelling device 7 are not shown in the drawing for the sake of simplicity.)

Figure 3:
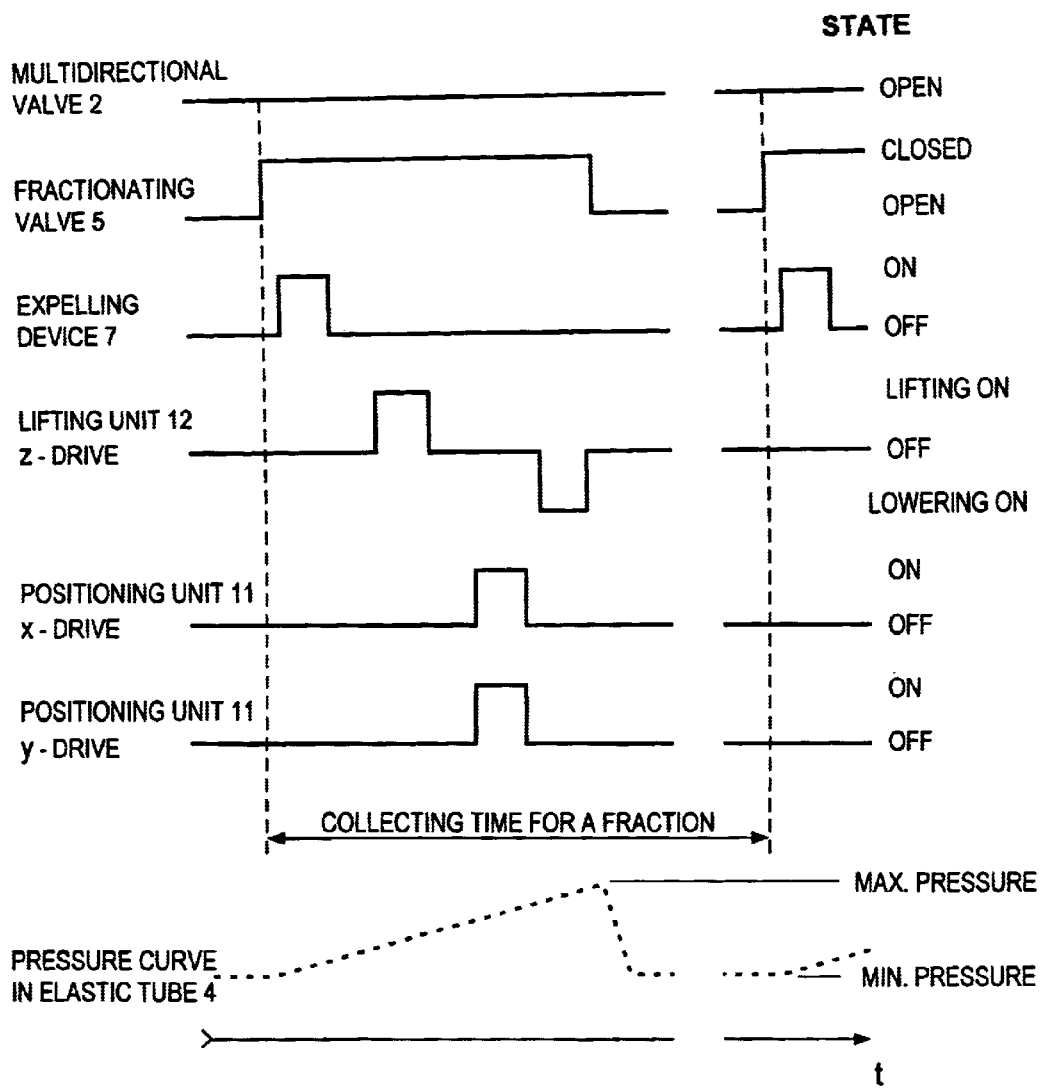
FIG. 3 shows a time flowchart for the control for the fraction collecting time with an impulse for expelling residual substance.
Figure 4:
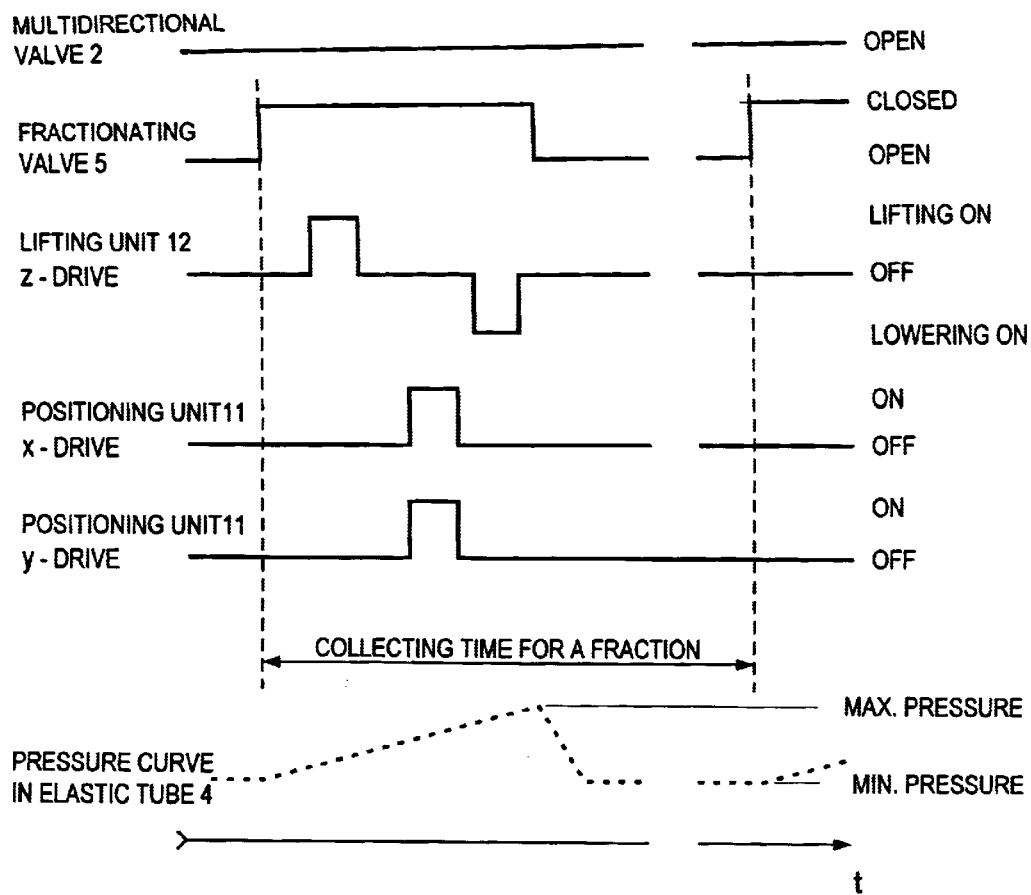
FIG. 4 shows a time flowchart for the control for the fraction collecting time without the impulse for expelling residual substance.

FIG. 3 shows a time flowchart relating to the fraction collecting time with an impulse of the type mentioned above for expelling residual drops of liquid (expelling device 7), for the control of the positioning unit 11, the lift unit 12 and the fractionating valve 5 and shows the pressure curve in the elastic tube 4. For purposes of comparison, FIG. 4 shows a relevant time flowchart without the impulse for the expelling residual drops.

Figure 5:
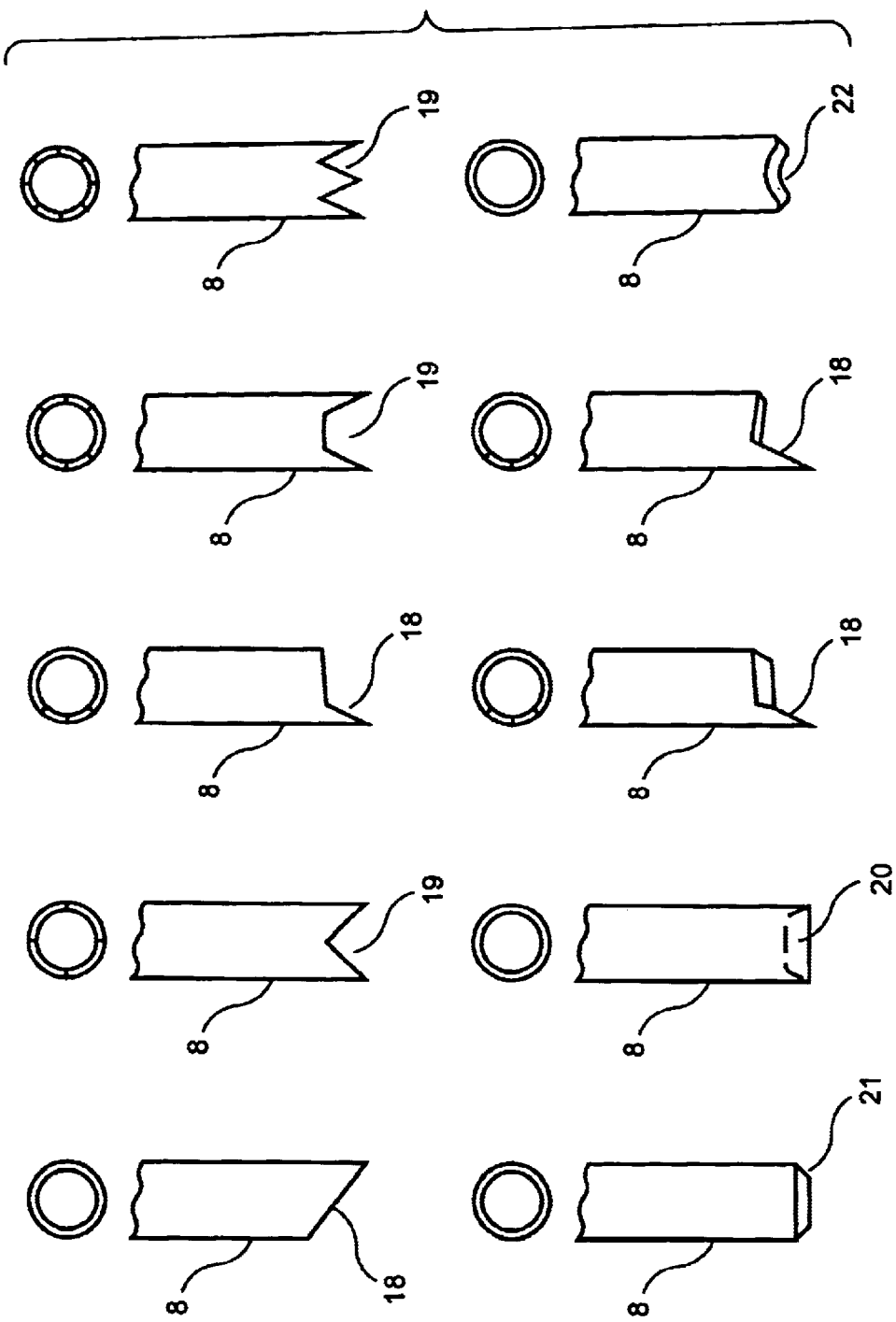
FIG. 5 shows embodiment forms of the hollow perforating tip.

FIG. 5 shows two views of possible embodiment forms for the perforating tip 8 piercing the cover foil 13. The invention is not limited to the forms shown herein. The perforating tip 8 can have, for example, individual tips 18, multiple tips 19, bevels 20, bezels 21, optionally shaped chamfers 22, etc. individually or in combination. Suitable perforating tip shapes are selected depending on the purpose for which they are used, particularly with respect to the type of cover foil 13 to be pierced.

In FIG. 6, additional cutters 23 of different shapes are arranged at the perforating tip 8 (FIGS. 6a to 6c show four cutters and FIGS. 6d to 6f show two cutters in two views, respectively). During the lifting movement of the perforating tip 8 into the collecting vessel 9, the cutters 23 slit the cover foil 13 with a single or multiple slit in addition to the perforation for dispensing the substance. While the collecting vessels 9 remain essentially covered by the cover foil 13 and retain the advantages of the invention mentioned above due to the slits, continued handling of the collected fractions by liquid handling devices, known per se, particularly multipipettes, is still possible in a simple manner without having to first remove the cover foil 13. The device elements can likewise penetrate into the collecting vessels 9 through the slits for handling specimens. The slit openings close again automatically after handling due to the flexible cover foil 13.

The cover foil 13 is advisably provided with adhesive locations only in the area of the surfaces contacting the multiwell analysis plate 10, so that the perforating tip 8 is not contaminated by the adhesive and the fractionated material is prevented from adhering to the perforating tip 8 due to the adhesive.

In order to fasten the perforating tip 8 to the lifting device 12 such that it can be exchanged quickly, but in a precisely positioned manner, with a low expenditure on handling and adjustment, the perforating tip 8 in FIG. 7 is provided with a receiving flange 24 for receiving in a clamping device 25 of the lifting device 12. The receiving flange 24 with the perforating tip 8 is inserted into the clamping device 25 up to the annular stop and is locked by turning the clamping screw 26. In this way, the perforating tip 8 can be changed in a fast and uncomplicated manner depending on the conditions of use, but the positioning accuracy required for exact vertical movement control (also with respect to wiping off residual liquid after the substance has been dispensed) is ensured at the same time. For all-purpose use, the perforating tip 8 and the feed system for supplying the liquid should be connected by plug-in connectors and quick couplings, etc. in order to realize a construction which can be made operational quickly and which, above all, can be converted or retrofitted. For example, perforating tips 8 and feed elements with different throughflow dimensions and quantities and, depending on the prerequisites for fractionation, particularly tubes 4, 17 with sizes and elasticity for varied uses can be fitted in a very short time.

Since the thin, hollow perforating tip 8 for dispensing substance, with its inner diameter of 0.5 mm or less and its outer diameter of 0.9 mm or less, is a very sensitive component part, especially with respect to bending stress, a sensor (not shown in the drawing) is inserted at the perforating tip 8 for detecting the bending load exerted on the perforating tip 8 during positioning, for example, in case of an unforeseen obstruction. In the event of damage, this sensor switches off the movement control. Further, moisture sensors (also not shown in the drawing) for detecting leaks under the tube system and under the multiwell analysis plate 10 are helpful for quickly switching off the device in order to prevent damage due to liquid losses.

FIG. 8 shows a comparison of the evaporation loss in a known commercially available multiwell analysis plate 10 measured at different temperatures in collecting vessels 9 of the multiwell analysis plate 10 which are open and collecting vessels 9 which are closed by the cover foil 13 and which are arranged in an 8×12 grid. The perforation of the cover foil 13 was simulated by vertical punctures over each collecting vessel 9 with a puncture hole having a diameter of approximately 0.5 mm. The collecting vessels 9 were filled with 150 μl of deionized water and were kept either at room temperature or on a copper plate cooled to 4° C. in a laboratory at room temperatures of 18 to 23° C. for a period of 18.4 hours. The evaporation was measured by measuring the weight before and after the experiment.

While the foregoing description and drawings represent the present invention, it will be obvious to those skilled in the art that various changes may be made therein without departing from the true spirit and scope of the present invention.

Reference numbers 1 connection adapter
2 multidirectional valve
3 control unit
4 elastic tube
5 fractionating valve
6 waste receptacle
7 expelling device
8 perforating tip
9 collecting vessel
10 multiwell analysis plate
11 positioning unit
12 lifting unit
13 cover foil
14 temperature regulating unit
15 plunger
16 abutment
17 tube
18 individual tip
19 multiple tip
20 bevel
21 bezel
22 chamfer
23 cutter
24 receiving flange
25 clamping device
26 clamping screw

What is claimed is:

1. A method for collecting fractions after material separation in which a substance-dispensing element is positioned over collecting vessels relative to the latter, which collecting vessels are arranged in a defined grid conformable to liquid handling technique, and is moved into the collecting position by a vertical relative movement, a substance quantity to be fractioned being dispensed in the selected collecting vessel in this collecting position, comprising the steps of:

perforating a cover which is located on each collecting vessel, which prevents the formation of aerosol in the environment, which closes so as to prevent evaporation and contamination, which expels residual drops at the substance-dispensing element and which protects against other substance proportions that would lead to faulty fractionation, said cover being perforated by the substance-dispensing element during its vertical relative movement for dispensing the substance, which substance-dispensing element dispenses the substance in the collection position through this cover into the selected collecting vessel and then moves out of the covered collecting vessel back into the starting position;

interrupting the flow of substance to the substance-dispensing element during the positioning movement of the substance-dispensing element; and elastically receiving and storing the substance temporarily in order to dampen the changes in pressure acting on the substance-dispensing element due to this interruption.

2. The method according to claim 1, wherein for purposes of further preventing faulty fractionation or substance entrainment the substance-dispensing element is moved into the selected collecting vessel until residual drops at the substance-dispensing element following the interruption of the liquid flow are wiped off by contact with the collected substance and/or the substance inserted beforehand or by contact with the inner wall of the collecting vessel.

3. The method according to claim 1, wherein the positioning movement of the substance-dispensing element is controlled in high-resolution steps.

4. The method according to claim 1, wherein for purposes of further preventing faulty fractionation or substance entrainment a residual liquid in the form of a drop on the substance-dispensing element after the substance has been dispensed in a selected collecting vessel is expelled by means of an impulse acting mechanically on the substance-dispensing element or on its feed.

5. The method according to claim 4, wherein the impulse is transmitted to an elastic element of the substance supply, for example, a feed tube.

6. The method according to claim 1, wherein the collecting vessels are temperature-regulated in order to further reduce the risk of evaporation and for more careful handling of the fractions.

7. The method according to claim 1, wherein the cover located on the collecting vessels is slit in addition to the perforation carried out by the substance-dispensing element for collection of fractions for purposes of continued handling of the collected fractions by liquid handling devices, known per se, without removing the cover.

8. A device for collecting fractions after material separation comprising apparatus, particularly a connection adapter and feed tube, for providing and feeding the substance to be fractionated, comprising:

a fractionating unit for the substance, which fractionating unit is constructed as a controlled valve, comprising a substance-dispensing element for dispensing the substance to be fractionated in collecting vessels which are arranged in a defined grid conformable to liquid handling technique, and comprising apparatus for moving the substance-dispensing element into position relative to the collecting vessels, including a lifting unit for lowering the substance-dispensing element to the selected collecting vessel;

a hollow perforating tip being provided as substance-dispensing element and serving to pierce a cover which is located on the collecting vesselsand which prevents the formation of aerosol in the environment, protects against evaporation and contamination, and protects against other substance proportions that would lead to faulty fractionation;

said substance-dispensing element also serving to dispense substance through this cover into the selected collecting vessel;

apparatus being provided for interrupting the supply of substance to the perforated tip during the positioning movement of the latter; and at least one elastic deformation body being provided for elastically receiving and temporarily storing the substance that is backed up due to the interruption of the substance supply.

9. The device according to claim 8, wherein the apparatus for interrupting the substance supply to the perforating tip is also provided for expelling residual drops located at the perforating tip after the substance has been dispensed by means of an impulse acting mechanically on the liquid in front of or in the perforating tip.

10. The device according to claim 8, wherein an electromagnetically controlled valve is provided as apparatus for interrupting the substance supply to the perforating tip during the positioning movement of the latter.

11. The device according to claim 8, wherein a flexible feed tube with a small inner diameter of less than 0.5 mm is provided as elastic deformation body.

12. The device according to claim 8, wherein a multiwell analysis plate, is provided as collecting vessels, wherein these collecting vessels which are arranged, for example, in a n×8×12 grid are closed by a foil.

13. The device according to claim 8, wherein the collecting vessels are closed by a foil which has adhesive exclusively at the support surfaces for the purpose of fastening the foil.

14. The device according to claim 8, wherein the collecting vessels communicate with a temperature-regulating unit, for example, a metal plate whose temperature can be regulated and which has Peltier elements or a water-cooled base plate, for regulating the temperature of the fractions contained in the collecting vessels.

15. The device according to claim 8, wherein the lifting device communicates with a high-resolution stepping drive for sensitive positioning of the perforating tip.

16. The device according to claim 8, wherein the perforating tip has a receptacle, such as a cylindrical flange with an annular stop, which is provided in a defined position for a clamping device for fastening to the lifting unit in an exchangeable, fast and precisely positioned manner.

17. The device according to claim 8, wherein at least one sensor for detecting the bending load of the perforating tip, is arranged at the perforating tip for protecting the perforating tip from mechanical loading in the event of an unforeseen obstruction, which sensor communicates with the apparatus for the positioning movement of the perforating tip and for substance supply, and which interrupts the positioning movement and substance supply.

18. The device according to claim 8, wherein sensors for detecting leaks are arranged below the collecting vessels and/or the liquid-conducting elements, particularly below the tubes, and wherein the sensors are coupled with a unit for switching off the installation.

19. The device according to claim 8, wherein the perforating tip comprises a material with high mechanical strength and high resistance to chemicals, for example, an inert high-quality steel, and in that its inner diameter is 0.5 mm or less and its outer diameter is 0.9 mm or less.

20. The device according to claim 8, wherein the perforating tip has an individual tip.

21. The device according to claim 8, wherein the perforating tip has a multiple tip.

22. The device according to claim 8, wherein the perforating tip has bevels or bezels.

23. The device according to claim 8, wherein the perforating tip has any curved bevel.

24. The device according to claim 8, wherein the perforating tip has one or more tips and/or at least one bevel.

25. The device according to claim 8, wherein at least the deformation body and the perforating tip have means for fast connection, for example, plug-in connectors or a fast coupling, for exchangeable use.

26. The device according to claim 8, wherein at least one cutter is provided in addition to the perforating tip, which cutter slits the cover so that fractions collected in the collecting vessels can be further handled by liquid handling devices, without having to remove the cover.

27. The device according to claim 26 wherein the at least one cutter is likewise arranged at the perforating tip or at the lifting device and, when the latter is positioned, is moved for slitting the cover.

* * * * *

UNITED STATES PATENT AND TRADEMARK OFFICE
CERTIFICATE OF CORRECTION

PATENT NO. : 6,698,470 B1
DATED : March 2, 2004
INVENTOR(S) : Anton Horn et al.

It is certified that error appears in the above-identified patent and that said Letters Patent is hereby corrected as shown below:

<u>Title page,</u>
Item [57], ABSTRACT,
Lines 1-17, please replace with the following:
-- The invention is directed to a method and a device for collecting microliter fractions after material separation for analytic and preparative applications, particularly in pharmaceutics, pharmacology, clinical analysis, biochemistry, molecular biology and biotechnology. Fractions are collected, preferably in the range of a few microliters, without risking impurities, evaporation losses, and mixing of fractions and with the least possible expenditure for prehandling and posthandling of the specimen vessels. According to the invention, the collecting vessels, preferably of a multiwell analysis plate, are closed and supplied with a cover foil, for example, an adhesive foil, which can be perforated. A perforating tip pierces the cover foil and dispenses a preadjusted volume, depending upon time, volume flow or upon a detector signal, through this cover foil into the appropriate collecting vessel. The collecting vessels remain closed during fractionation, so that aerosol formation, evaporation losses, contamination of the fractionated specimens by dust particles and other dirt particles, faulty fractionation and entrainment of fractions are reliably prevented. Additionally, the cover foil can be slit to allow further handling by liquid handling devices, known per se. During the positioning movement of the perforating tip, the volume flow of the substance to be fractionated is interrupted and elastically received by a deformation body. --

Signed and Sealed this

Tenth Day of August, 2004

JON W. DUDAS
*Acting Director of the United States Patent and Trademark Office*